(12) United States Patent
Rao et al.

(10) Patent No.: US 9,018,376 B2
(45) Date of Patent: Apr. 28, 2015

(54) POLYMORPHIC FORMS OF MANIDIPINE

(75) Inventors: Dharmaraj Ramachandra Rao, Maharashtra (IN); Rajendra Narayanrao Kankan, Maharashtra (IN); Maruti Ganpati Ghagare, Maharashtra (IN)

(73) Assignee: Cipla Limited, Mumbai (IN)

( * ) Notice: Subject to any disclaimer, the term of this patent is extended or adjusted under 35 U.S.C. 154(b) by 458 days.

(21) Appl. No.: 13/392,583

(22) PCT Filed: Aug. 26, 2010

(86) PCT No.: PCT/GB2010/001615
§ 371 (c)(1), (2), (4) Date: May 3, 2012

(87) PCT Pub. No.: WO2011/023954
PCT Pub. Date: Mar. 3, 2011

(65) Prior Publication Data
US 2012/0232091 A1 Sep. 13, 2012

(30) Foreign Application Priority Data
Aug. 27, 2009 (IN) .................. 1970/MUM/2009

(51) Int. Cl.
*C07D 211/90* (2006.01)
*A61K 31/496* (2006.01)

(52) U.S. Cl.
CPC ............ *C07D 211/90* (2013.01); *A61K 31/496* (2013.01)

(58) Field of Classification Search
CPC ..................................... C07D 401/12
USPC ..................... 514/253.01; 544/360
See application file for complete search history.

(56) References Cited

U.S. PATENT DOCUMENTS

| | | | |
|---|---|---|---|
| 4,892,875 A | 1/1990 | Meguro et al. | |
| 4,994,461 A | 2/1991 | Ulrich | |

FOREIGN PATENT DOCUMENTS

| | | |
|---|---|---|
| EP | 0094159 B1 | 3/1990 |
| FR | 2924223 A1 | 5/2009 |
| WO | 8807525 A1 | 10/1988 |
| WO | 2011023954 A2 | 3/2011 |

OTHER PUBLICATIONS

Foreign communication from the priority application—International Search Report, PCT/GB2010/001615 issued on Feb. 25, 2011, 6 pages.
Hosaka, Shouichi, et al., "Effect of Compression on Interaction Between 1,4-Dihydropyridine Compounds and Lactose Monohydrate," Pharm. Bull., May 2005, pp. 503-507, vol. 53, No. 5, Pharmaceutical Society of Japan.
Kajino, Masahiro, et al., "Synthesis and Biological Activities of Optical Isomers of 2-(4-Diphenylmethyl-1-piperazinyl) ethyl Methyl 1,4-Dihydro-2,6-dimethyl-4-(3-nitrophenyl)-3,5-pyridinedicarboxylate (Manidipine$^1$) Dihydro-chloride," Chem. Pharm Bull., Aug. 1989, pp. 2225-2228, vol. 37, No. 8, Pharmaceutical Society of Japan.
Leonardi, Amedeo, et al., "Asymmetric N-(3,3-diphenylpropyl)aminoalkyl esters of 4-aryl-2,6-dimethyl-1,4-dihydropyridine-3,5-dicarboxylic acids with antihypertensive activity," Eur. J. Med. Chem., 1998, pp. 399-420, vol. 33, Elsevier, Paris.
Meguro, Kanji, et al., "New 1,4-Dihydropyridine Derivatives with Potent and Long-Lasting Hypotensive Effect," Chem. Pharm. Bull, 1985, XP000602167, pp. 3787-3797, vol. 33, No. 9.
Ragno, Gaetano, et al., "Multivariate Least Squares Regression Applied to the Spectrophotometric Analysis of Manidipine and Its Main Photoproduct," II Farmaco, 2003, XP002621864, pp. 909-915, vol. 58, Elsevier.

*Primary Examiner* — Rebecca Anderson
*Assistant Examiner* — Karen Cheng
(74) *Attorney, Agent, or Firm* — Conley Rose, P.C.; Rodney B. Carroll

(57) ABSTRACT

The invention relates to various new polymorphic forms of manidipine and pharmaceutically acceptable salts thereof. The invention also relates to processes for the preparation of the polymorphic forms of manidipine and pharmaceutically acceptable salts thereof.

5 Claims, 7 Drawing Sheets

POLYMORPHIC FORMS OF MANIDIPINE

CROSS-REFERENCE TO RELATED APPLICATIONS

This application is a filing under 35 U.S.C. 371 of International Application No. PCT/GB2010/001615 filed Aug. 26, 2010, entitled "Polymorphic Forms of Manidipine," claiming priority of Indian Patent Application No. 1970/MUM/2009 filed Aug. 27, 2009, which applications are incorporated by reference herein in their entirety.

FIELD OF THE INVENTION

The present invention relates to novel polymorphic forms of a calcium channel blocker and processes for their preparation.

In particular, the present invention relates to novel polymorphic forms of manidipine and pharmaceutically acceptable salts thereof. The invention also relates to processes for preparation of said novel polymorphs.

BACKGROUND

Manidipine, chemically described as 1,4-dihydro-2,6-dimethyl-4-(3-nitrophenyl)-3,5-pyridinedicarboxylic acid 2-[4-(diphenylmethyl)-1-piperazinyl]ethyl methyl ester is a dihydropyridine calcium channel blocker. It is also known as franidipine and represented by the structure (I) shown below.

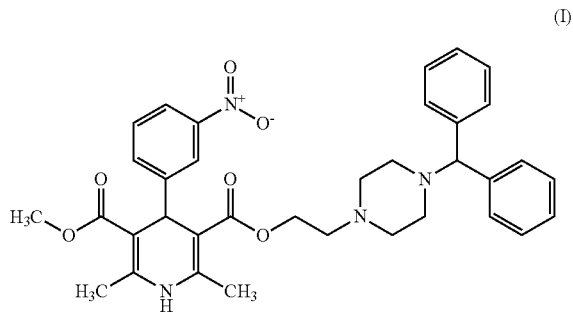 [SMILES: COC(=O)C1=C(C)NC(C)=C(C(=O)OCCN2CCN(C(c3ccccc3)c3ccccc3)CC2)C1c1cccc([N+](=O)[O-])c1]

(I)

Manidipine is a lipophilic and highly vasoselective agent and has long-lasting activity for the treatment of hypertension. Manidipine is a dihydropyridine (DHP) calcium channel antagonist, which effectively reduces blood pressure in patients with mild-to-moderate hypertension and effectively maintains reduced blood pressure levels throughout the dosing period of 24-hours. It is effective in the long term with no evidence of intolerance. Manidipine provides a first-line option for lowering blood pressure in patients with mild-to-moderate hypertension.

The preparation of manidipine and its existence in polymorphic forms is described in EP0094159B1 and its equivalent U.S. Pat. No. 4,892,875. Also, Chem. Pharm. Bull., 1989, 37, (8), 2225-8 describes the synthesis of enantiomeric (+)- and (−)-manidipine dihydrochlorides by esterification of optically active monocarboxylic acids.

Chem. Pharm. Bull., 1985, 33, (9), 3787-3797 discloses two crystalline forms of manidipine dihydrochloride: the α form and the β form, characterized by melting points.

Further, the literature data also shows that manidipine can exist in crystalline base as well as manidipine dihydrochloride monohydrate forms.

Eur. J. Med. Chem., 33, 1998, 399-420 discloses manidipine, but gives no characterisation data.

FR 2924223 discloses a method of determine polymorphic purity of manidipine dihydrochloride using Raman spectra. This can be used to prepare manidipine dihydrochoride having predetermined polymorphic purity.

Consequently, it would be a significant contribution to the art to provide a crystalline form of manidipine and pharmaceutically acceptable salts thereof; having increased solubility, and methods of preparation, pharmaceutical formulations, and methods of use thereof.

OBJECTS OF THE INVENTION

An object of the present invention is to provide various polymorphic forms of manidipine and pharmaceutically acceptable salts thereof.

Another object of the present invention is to provide processes for the preparation of novel polymorphic forms of manidipine and pharmaceutically acceptable salts thereof.

Yet another object of the invention is to provide an industrially advantageous, cost effective and environmentally friendly process for preparing highly pure manidipine in high yields.

SUMMARY OF THE INVENTION

Figure 1:
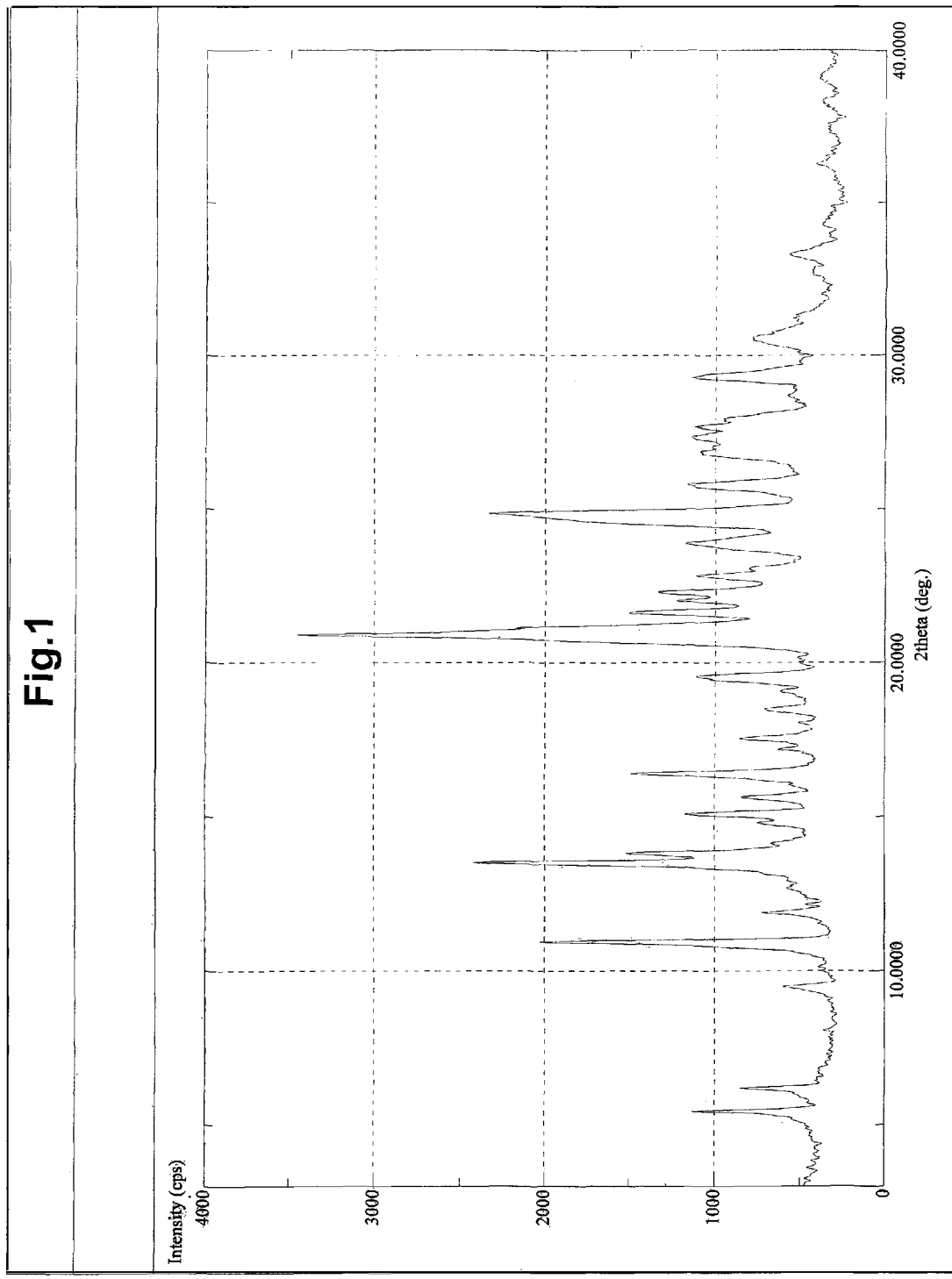
FIG. 1 shows an X-ray diffraction spectrum of form I of manidipine dihydrochloride.

The present invention provides novel polymorphic forms of manidipine dihydrochloride and base, referred to as Form I, Form II, Form III, Form IV, Form V, Form VI and Form VII.

Accordingly, the invention also provides methods for preparing these novel forms in high purity and high yield.

Each of the new forms is differentiated by a unique powder X-ray diffraction pattern.

The present invention further provides pharmaceutical compositions comprising novel manidipine forms I to VII together with one or more pharmaceutically acceptable excipients.

The invention also provides methods for preparing pharmaceutical composition comprising novel manidipine forms I to VII.

The present invention further provides method of treatment of diseases or symptoms wherein manidipine and pharmaceutically acceptable salts thereof, are useful.

The advantages of the process include simplicity, eco-friendliness and suitability for commercial use.

DETAILED DESCRIPTION OF THE INVENTION

The present invention provides novel crystalline forms of manidipine and pharmaceutically acceptable salts thereof, methods of preparing the novel forms of manidipine and pharmaceutically acceptable salts thereof in high purity and high yield and pharmaceutical compositions comprising them. The advantages of the process include simplicity, eco-friendliness and suitability for commercial use.

As polymorphic forms are most reliably characterized primarily by peak positions in the X-ray diffractogram, the polymorphs of the present invention have been characterized by powder X-ray diffraction spectroscopy which produces a fingerprint of the particular crystalline form. Measurements of 2θ values typically are accurate to within ±0.2 degrees. All the powder diffraction patterns were measured on a Rigaku Dmax 2200 advanced X-ray powder diffractometer with a copper-K-α radiation source. The XRD pattern is expressed in terms of 2 theta values (2θ) and percentage intensity (%).

All the polymorphs obtained in the present invention are stable, highly pure and with low amounts of residual solvents.

The invention further provides processes for the preparation of polymorphs.

Thus, in one aspect the present invention provides a novel polymorphic form of manidipine dihydrochloride which is hereinafter designated as 'Form I' which is substantially non-hygroscopic and has good flow characteristics.

In another aspect, the present invention provides a process for preparing the novel form I of manidipine dihydrochloride in high yield and purity. The present invention also provides pharmaceutical compositions comprising Form I of manidipine dihydrochloride.

In an embodiment, the process involves isolation of the Form I of manidipine dihydrochloride in a solvent-free media, thus producing manidipine dihydrochloride free of solvents or having a negligible solvent content.

In an embodiment, the crystalline polymorph Form I of manidipine dihydrochloride has an XRD pattern with peaks at 10.94, 13.50, 20.90, 21.14 and 24.86±0.2°2θ. The XRD pattern may comprise further peaks at 13.82 16.40, 20.72, 24.50 and 24.58 °2θ±0.2 °2θ.

In an embodiment, the crystalline polymorph Form I of manidipine dihydrochloride has an XRD pattern with peaks at 2θ-values as shown in Table 1.

TABLE 1

| Diffraction angle (2θ-values) | Intensity (%) |
|---|---|
| 5.44 | 27 |
| 6.18 | 17 |
| 9.48 | 12 |
| 10.94 | 61 |
| 11.88 | 14 |
| 13.50 | 68 |
| 13.82 | 35 |
| 14.8 | 11 |
| 15.08 | 26 |
| 16.40 | 38 |
| 17.52 | 16 |
| 19.42 | 21 |
| 19.56 | 25 |
| 20.72 | 49 |
| 20.90 | 100 |
| 21.14 | 51 |
| 21.62 | 27 |
| 22.00 | 17 |
| 22.30 | 22 |
| 22.82 | 18 |
| 23.86 | 22 |
| 24.50 | 32 |
| 24.58 | 42 |
| 24.86 | 61 |
| 25.70 | 21 |
| 25.80 | 23 |
| 26.76 | 16 |

TABLE 1-continued

| Diffraction angle (2θ-values) | Intensity (%) |
|---|---|
| 26.86 | 16 |
| 27.30 | 17 |
| 27.68 | 17 |
| 29.26 | 24 |
| 29.38 | 21 |

In another embodiment, the X-ray powder diffraction spectrum of crystalline polymorphic Form I of manidipine dihydrochloride is depicted in FIG. 1.

According to another aspect of the present invention, there is provided a process for preparation of Form I, comprising dissolving manidipine dihydrochloride in methanol at reflux, cooling the reaction mass to a temperature ranging from about 25° C. to 30° C., isolating the precipitated crystalline Form I of manidipine dihydrochloride and drying under vacuum at about 40-45° C. for at least 10 hours. The crystalline Form I of manidipine dihydrochloride prepared by the process may be in the form as described above.

In a preferred embodiment, the Form I manidipine dihydrochloride is provided in the form of a racemate.

Another aspect the present invention provides a novel polymorphic form of manidipine dihydrochloride which is hereinafter designated as 'Form II' which is substantially non-hygroscopic and has good flow characteristics.

In another aspect, the present invention provides a process for preparing the novel form II of manidipine dihydrochloride in high yield and purity. The present invention also provides pharmaceutical compositions comprising Form II of manidipine dihydrochloride.

In an embodiment, the process involves isolation of the Form II of manidipine dihydrochloride in a solvent-free media, thus producing manidipine dihydrochloride free of solvents or having a negligible solvent content.

In an embodiment, Form II of the present invention is characterized by X-ray powder diffraction spectrum comprising peaks at 10.94, 22.02, 22.74 and 22.84±0.2 °2θ. The XRD pattern may comprise further peaks at 13.5, 17.52 and 21.02±0.2 °2θ.

In an embodiment, the crystalline polymorph 'Form II' of manidipine dihydrochloride has an XRD pattern with peaks at 2θ-values as shown in Table 2.

TABLE 2

| Diffraction angle (2θ-values) | Intensity (%) |
|---|---|
| 5.46 | 26 |
| 8.06 | 8 |
| 10.12 | 10 |
| 10.94 | 81 |
| 11.88 | 8 |
| 12.66 | 7 |
| 13.50 | 37 |
| 13.98 | 10 |
| 14.78 | 23 |
| 16.20 | 17 |
| 17.52 | 46 |
| 18.06 | 12 |
| 19.06 | 14 |
| 20.16 | 15 |
| 20.64 | 9 |
| 21.02 | 49 |
| 22.02 | 53 |
| 22.50 | 18 |
| 22.74 | 69 |
| 22.84 | 100 |
| 23.72 | 11 |
| 24.08 | 12 |

TABLE 2-continued

| Diffraction angle (2θ-values) | Intensity (%) |
|---|---|
| 24.44 | 9 |
| 24.86 | 18 |
| 25.56 | 17 |
| 26.40 | 15 |
| 27.72 | 19 |
| 28.10 | 16 |
| 30.60 | 10 |

Figure 2:
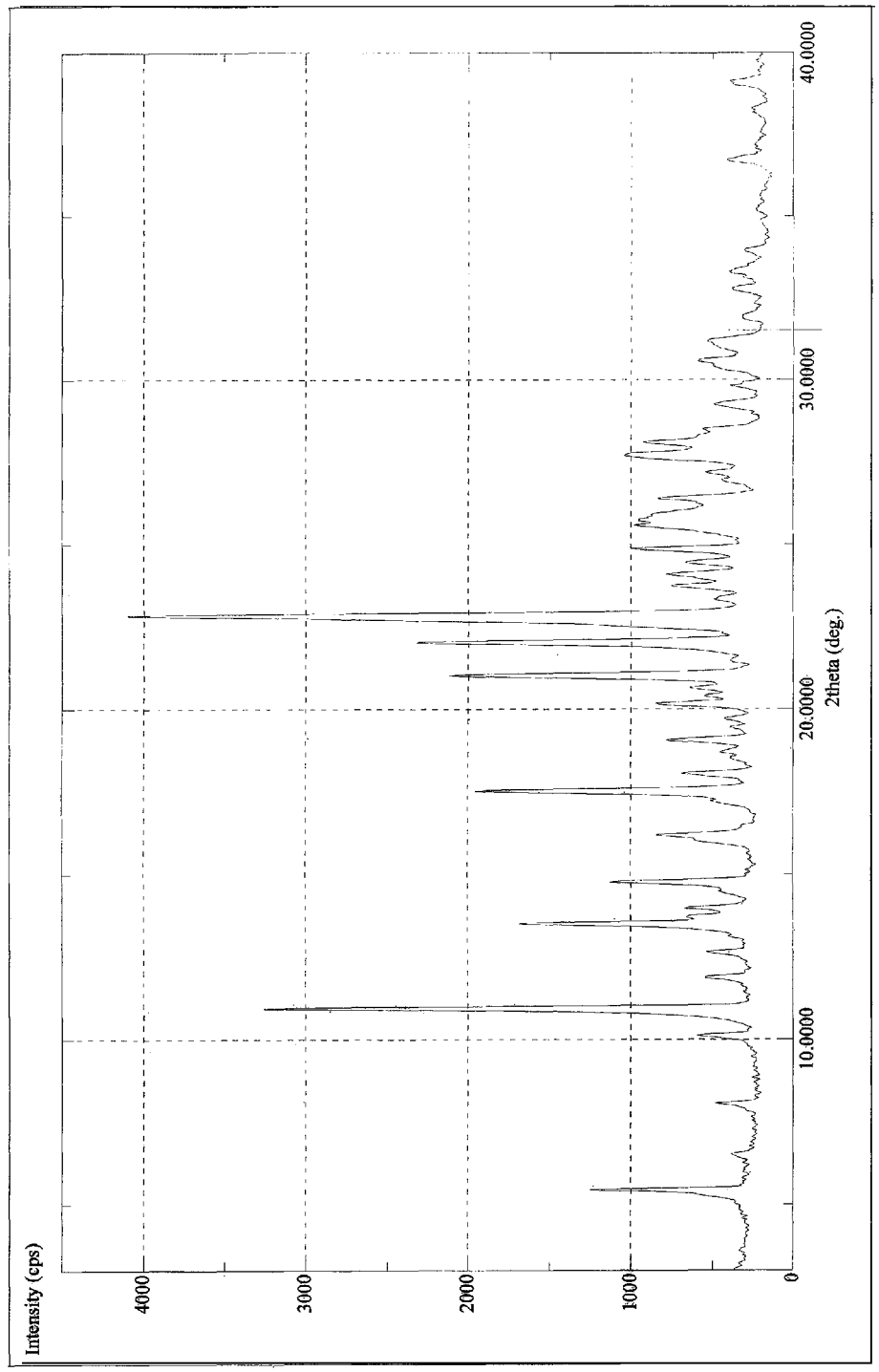
FIG. 2 shows an X-ray diffraction spectrum of form II of manidipine dihydrochloride.

In another embodiment, the X-ray powder diffraction spectrum of crystalline polymorphic Form II of manidipine dihydrochloride is depicted in FIG. 2.

According to another aspect of the present invention, there is provided a process for preparation of Form II, comprising dissolving manidipine dihydrochloride in a mixture of methanol and denatured ethanol (1:1) at reflux, cooling the reaction mass to a temperature ranging from about 25° C. to 30° C., stirring for 12-14 hours, isolating the precipitated crystalline Form II of manidipine dihydrochloride and drying under vacuum at about 40-45° C. for at least 10 hours. The crystalline Form II of manidipine dihydrochloride prepared by the process may be in the form as described above.

In a preferred embodiment, the Form II manidipine dihydrochloride is provided in the form of a racemate.

Yet another aspect the present invention provides a novel polymorphic form of manidipine dihydrochloride which is hereinafter designated as 'Form III' which is substantially non-hygroscopic and has good flow characteristics.

In another aspect, the present invention provides a process for preparing the novel Form III of manidipine dihydrochloride in high yield and purity. The present invention also provides pharmaceutical compositions comprising Form III of manidipine dihydrochloride.

In an embodiment, the process involves isolation of the Form III of manidipine dihydrochloride in a solvent-free media, thus producing manidipine dihydrochloride free of solvents or having a negligible solvent content.

In an embodiment, Form III of the present invention is characterized by X-ray powder diffraction spectrum comprising peaks at 9.06, 13.44, 20.98, 21.70, 21.80, 21.92, 22.80 and 24.42±0.2 °2θ. The XRD pattern may comprise further peaks at 10.90, 14.28, 15.80, 18.28, 27.60 and 27.70±0.2 °2θ.

In an embodiment, the crystalline polymorph Form III of manidipine dihydrochloride has an XRD pattern with peaks at 2θ-values as shown in Table 3.

TABLE 3

| Diffraction angle (2θ-values) | Intensity (%) |
|---|---|
| 5.80 | 25 |
| 6.70 | 19 |
| 9.06 | 72 |
| 10.90 | 30 |
| 11.84 | 18 |
| 13.44 | 51 |
| 14.28 | 36 |
| 15.80 | 36 |
| 16.14 | 19 |
| 17.50 | 23 |
| 18.00 | 20 |
| 18.28 | 31 |
| 20.98 | 100 |
| 21.70 | 55 |
| 21.80 | 65 |
| 21.92 | 67 |
| 22.80 | 57 |
| 24.02 | 29 |

TABLE 3-continued

| Diffraction angle (2θ-values) | Intensity (%) |
|---|---|
| 24.42 | 57 |
| 24.80 | 25 |
| 25.76 | 28 |
| 26.34 | 24 |
| 27.60 | 37 |
| 27.70 | 41 |
| 28.10 | 28 |
| 28.24 | 22 |

Figure 3:
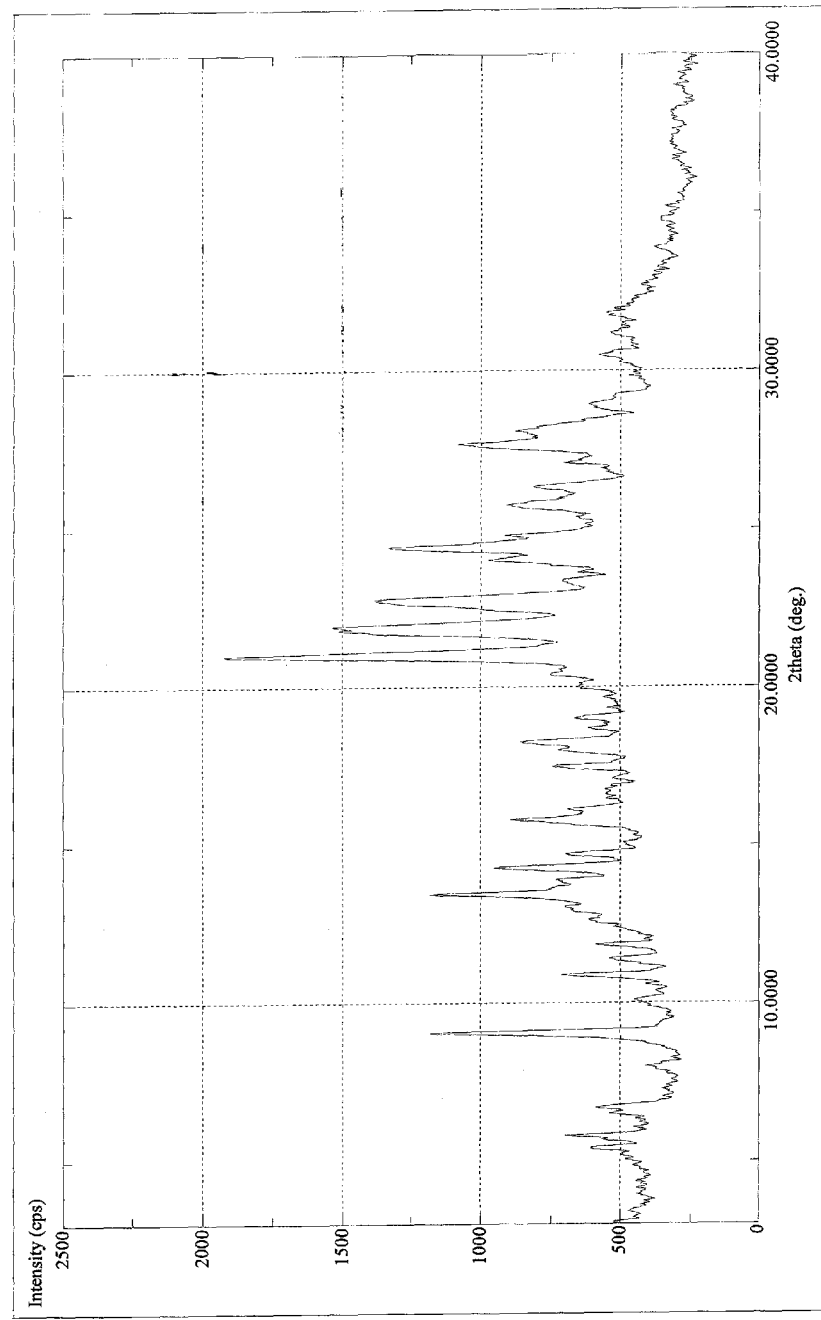
FIG. 3 shows an X-ray diffraction spectrum of form III of manidipine dihydrochloride.

In another embodiment, the X-ray powder diffraction spectrum of crystalline polymorphic Form III of manidipine dihydrochloride is depicted in FIG. 3.

According to another aspect of the present invention, there is provided a process for preparation of Form III, comprising dissolving manidipine dihydrochloride in a mixture of methanol and toluene (1:1) at 75-80° C., cooling the reaction mass to a temperature ranging from about 25° C. to 30° C., stifling for 12-14 hours, isolating the precipitated crystalline Form III of manidipine dihydrochloride and drying under vacuum at about 40-45° C. for at least 10 hours. The crystalline Form III of manidipine dihydrochloride prepared by the process may be in the form as described above.

In a preferred embodiment, the Form III manidipine dihydrochloride is provided in the form of a racemate.

Yet another aspect, the present invention provides a novel polymorphic form of manidipine dihydrochloride which is hereinafter designated as 'Form IV' which is substantially non-hygroscopic and has good flow characteristics.

In another aspect, the present invention provides a process for preparing the novel form IV of manidipine dihydrochloride in high yield and purity. The present invention also provides pharmaceutical compositions comprising Form IV of manidipine dihydrochloride.

In an embodiment, the process involves isolation of the Form IV of manidipine dihydrochloride in a solvent-free media, thus producing manidipine dihydrochloride free of solvents or having a negligible solvent content.

In an embodiment, Form IV of the present invention is characterized by X-ray powder diffraction spectrum comprising peaks at 12.58, 20.34 and 23.36±0.2 °2θ. The XRD pattern may comprise further peaks at 7.90, 10.10, 18.98, 22.28, 26.62 and 28.32±0.2 °2θ.

In an embodiment, the crystalline polymorph Form IV of manidipine dihydrochloride has an XRD pattern with peaks at 2θ-values as shown in Table 4.

TABLE 4

| Diffraction angle (2θ-values) | Intensity (%) |
|---|---|
| 5.60 | 16 |
| 6.22 | 29 |
| 7.90 | 32 |
| 10.10 | 39 |
| 11.14 | 21 |
| 12.58 | 87 |
| 14.60 | 19 |
| 14.92 | 13 |
| 15.20 | 14 |
| 15.90 | 14 |
| 16.58 | 13 |
| 16.66 | 16 |
| 18.02 | 21 |
| 18.86 | 24 |
| 18.98 | 32 |
| 20.34 | 100 |
| 20.98 | 21 |

TABLE 4-continued

| Diffraction angle (2θ-values) | Intensity (%) |
|---|---|
| 22.00 | 24 |
| 22.28 | 41 |
| 23.36 | 61 |
| 23.92 | 18 |
| 25.10 | 18 |
| 25.34 | 29 |
| 26.62 | 34 |
| 27.64 | 13 |
| 28.32 | 46 |
| 30.14 | 18 |
| 30.74 | 13 |
| 33.24 | 13 |

Figure 4:
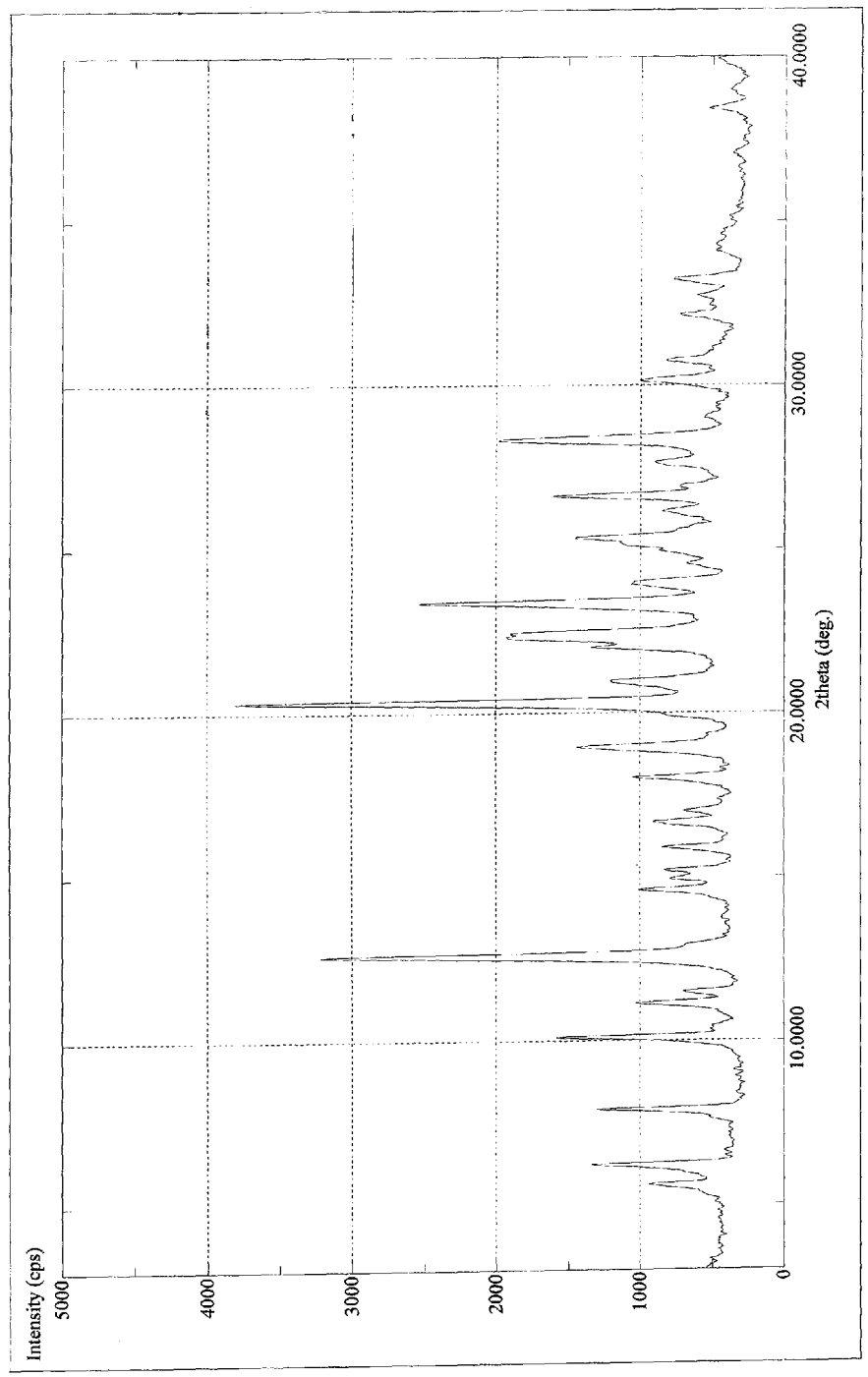
FIG. 4 shows an X-ray diffraction spectrum of form IV of manidipine dihydrochloride.

In another embodiment, the X-ray powder diffraction spectrum of crystalline polymorphic Form IV of manidipine dihydrochloride is depicted in FIG. 4.

According to another aspect of the present invention, there is provided a process for preparation of Form IV, comprising dissolving manidipine dihydrochloride in a mixture of toluene and denatured ethanol (1:1) at 75-80° C., cooling the reaction mass to a temperature ranging from about 25° C. to 30° C., stirring for 12-14 hours, isolating the precipitated crystalline Form IV of manidipine dihydrochloride and drying under vacuum at about 40-45° C. for at least 10 hours. The crystalline Form IV of manidipine dihydrochloride prepared by the process may be in the form as described above.

In a preferred embodiment, the Form IV manidipine dihydrochloride is provided in the form of a racemate.

In still another aspect the present invention, there is provided an amorphous form of manidipine dihydrochloride which is hereinafter designated as 'Form V' which is substantially non-hygroscopic and has good flow characteristics.

In another aspect, the present invention provides a process for preparing the novel form V of manidipine dihydrochloride in high yield and purity. The present invention also provides pharmaceutical compositions comprising Form V of manidipine dihydrochloride.

In an embodiment, the process involves isolation of the Form V of manidipine dihydrochloride in a solvent-free media, thus producing manidipine dihydrochloride free of solvents or having a negligible solvent content.

In an embodiment, Form V of the present invention is characterized by X-ray powder diffraction spectrum.

Figure 5:
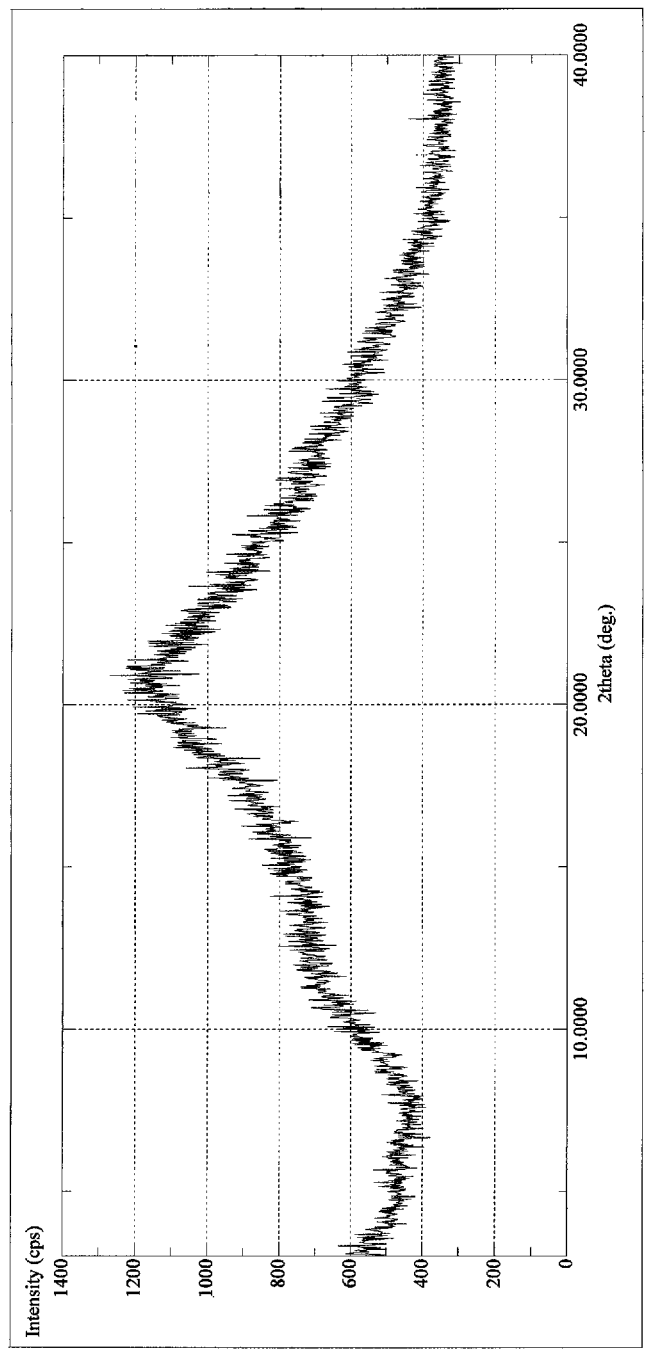
FIG. 5 shows an X-ray diffraction spectrum of amorphous form V of manidipine dihydrochloride.

In another embodiment, an amorphous Form V of manidipine dihydrochloride is characterized by having an XRD pattern as shown in FIG. 5.

According to another aspect of the present invention, there is provided a process for preparation of Form V, comprising dissolving manidipine dihydrochloride in methanol at reflux, concentrating under vacuum to dryness, isolating the precipitated amorphous Form V of manidipine dihydrochloride and drying under vacuum at about 40-45° C. for at least 10 hours. The amorphous Form V of manidipine dihydrochloride prepared by the process may be in the form as described above.

In a preferred embodiment, the Form V manidipine dihydrochloride is provided in the form of a racemate.

The manidipine dihydrochloride used in the preparation of the Forms I, II, III, IV or V, may be in any polymorphic form or in a mixture of any polymorphic forms.

In yet another aspect, the present invention provides a crystalline form of manidipine base which is hereinafter designated as 'Form VI' which is substantially non-hygroscopic and has good flow characteristics.

In another aspect, the present invention provides a process for preparing the novel form VI of manidipine base in high yield and purity. The present invention also provides pharmaceutical compositions comprising Form VI of manidipine base.

In an embodiment, the process involves isolation of the Form VI of manidipine base in a solvent-free media, thus producing manidipine base free of solvents or having a negligible solvent content.

In an embodiment, Form VI of the present invention is characterized by X-ray powder diffraction spectrum comprising peaks at 5.08, 14.04, 15.40, 20.60 and 21.94±0.2 °2θ. The XRD pattern may comprise further peaks at 15.08, 18.96, 19.44 and 22.26±0.2 °2θ.

In an embodiment, the crystalline polymorph Form VI of manidipine base has an XRD pattern with peaks at 2θ-values as shown in Table 5.

TABLE 5

| Diffraction angle (2θ-values) | Intensity (%) |
|---|---|
| 5.08 | 51 |
| 10.94 | 25 |
| 12.36 | 15 |
| 13.52 | 21 |
| 13.78 | 27 |
| 14.04 | 59 |
| 14.28 | 13 |
| 15.08 | 42 |
| 15.40 | 58 |
| 15.80 | 19 |
| 16.04 | 16 |
| 17.88 | 12 |
| 18.42 | 18 |
| 18.62 | 21 |
| 18.96 | 44 |
| 19.44 | 34 |
| 20.24 | 21 |
| 20.60 | 56 |
| 21.94 | 100 |
| 22.26 | 42 |
| 22.82 | 7 |
| 23.84 | 7 |
| 24.16 | 11 |
| 24.82 | 20 |
| 25.90 | 11 |
| 26.30 | 9 |
| 27.24 | 8 |
| 28.92 | 11 |
| 30.34 | 13 |
| 31.86 | 7 |
| 37.32 | 7 |

Figure 6:
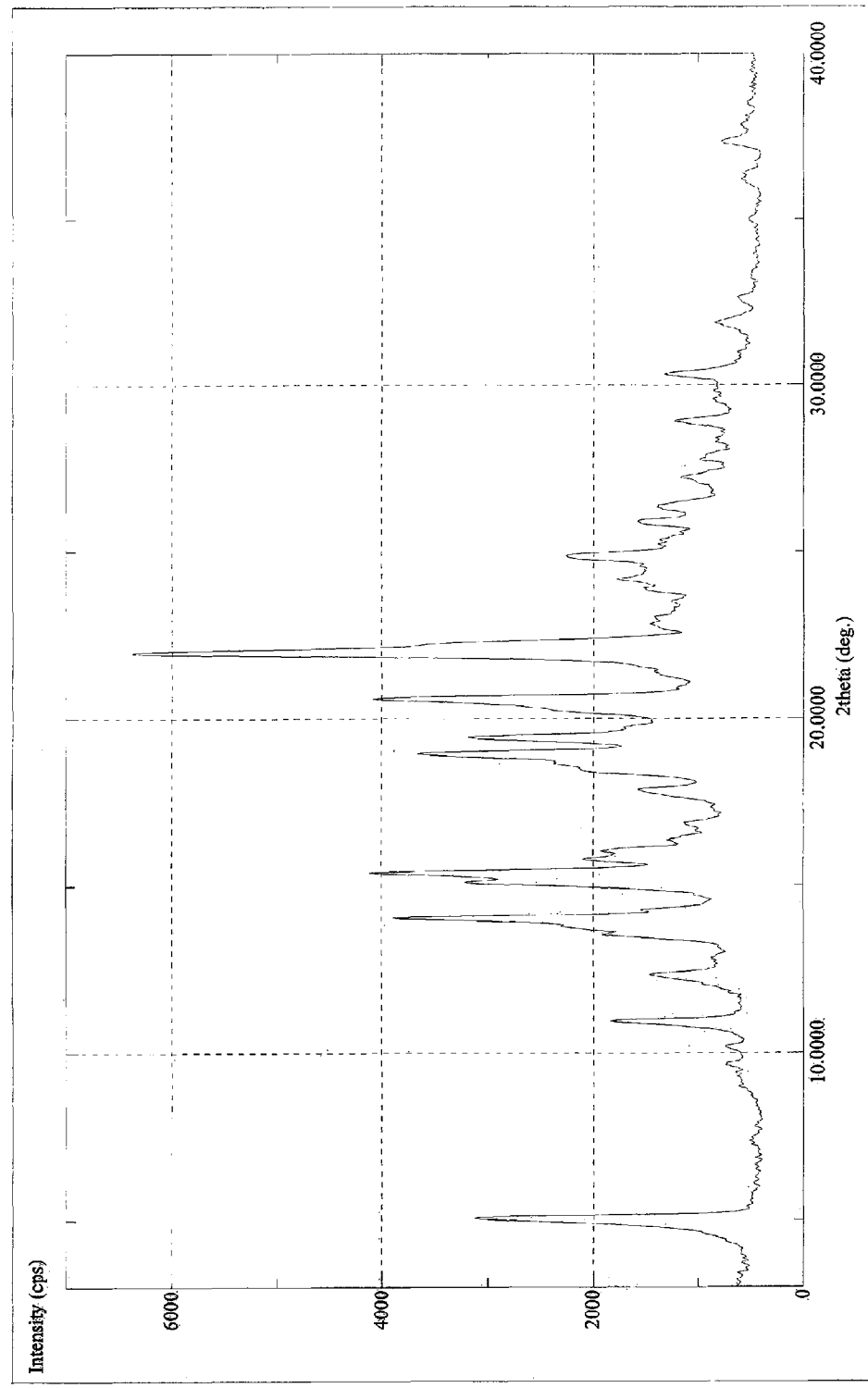
FIG. 6 shows an X-ray diffraction spectrum of form VI of manidipine base.

In another embodiment, crystalline Form VI of manidipine base is characterized by having an XRD pattern as shown in FIG. 6.

According to another aspect of the present invention, there is provided a process for preparation of Form VI, comprising dissolving manidipine base in methanol at reflux, cooling the reaction mass to a temperature ranging from about 25° C. to 30° C., adding n-Heptane under stirring, stirring for 10-12 hours, isolating the precipitated crystalline Form VI of manidipine base and drying under vacuum at about 40-45° C. for at least 10 hours. The crystalline Form VI of manidipine base prepared by the process may be in the form as described above.

In a preferred embodiment, the Form VI manidipine base is provided in the form of a racemate.

In still another aspect, the present invention provides an amorphous form of manidipine base which is hereinafter designated as 'Form VII' which is substantially non-hygroscopic and has good flow characteristics.

In another aspect, the present invention provides a process for preparing the novel Form VII of manidipine base in high yield and purity. The present invention also provides pharmaceutical compositions comprising Form VII of manidipine base.

In an embodiment, the process involves isolation of the Form VII of manidipine base in a solvent-free media, thus producing manidipine base free of solvents or having a negligible solvent content.

In an embodiment, Form VII of the present invention is characterized by X-ray powder diffraction spectrum.

Figure 7:
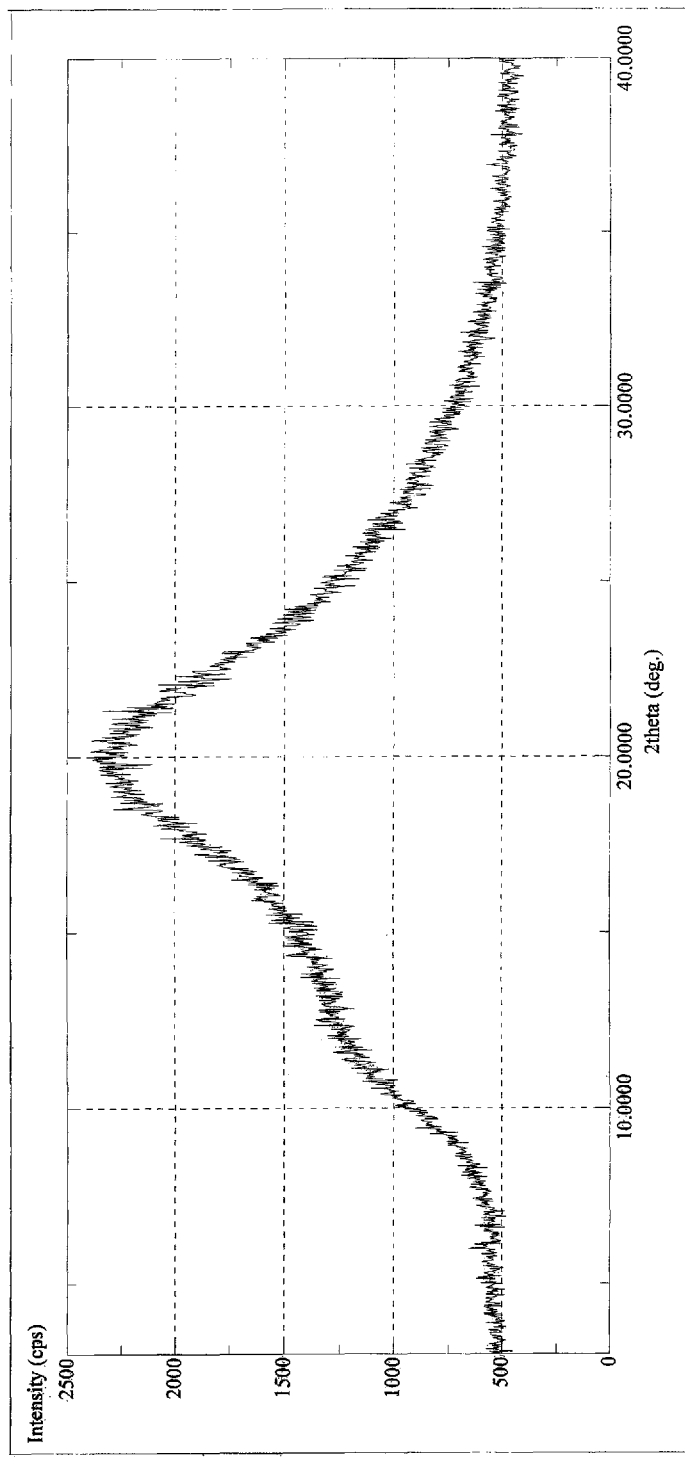
FIG. 7 shows an X-ray diffraction spectrum of amorphous form VII of manidipine base.

In another embodiment, amorphous Form VII of manidipine base is characterized by having an XRD pattern as shown in FIG. 7.

According to another aspect of the present invention, there is provided a process for preparation of Form VII, comprising dissolving manidipine base in methylene dichloride at about 40° C., concentrating under vacuum to dryness, isolating the precipitated Amorphous Form VII of manidipine base and drying under vacuum at about 40-45° C. for at least 10 hours. The amorphious Form VII of manidipine base prepared by the process may be in the form as described above.

In a preferred embodiment, the Form VII manidipine base is provided in the form of a racemate.

The manidipine base used in the preparation of the Forms VI or VII may be in any polymorphic form or in a mixture of any polymorphic forms.

The novel polymorphs of manidipine obtained according to the present invention is substantially free from other forms of manidipine. "Substantially free" from other forms of manidipine shall be understood to mean that the polymorphs of manidipine contain less than 10%, preferably less than 5%, of any other forms of manidipine and less than 1% of other impurities, water or solvates.

The process of invention may be used as a method for purifying any form of manidipine, as well as for the preparation of the new polymorphic forms.

According to another aspect of the present invention, there is provided a pharmaceutical composition comprising polymorphic Forms of manidipine or pharmaceutically acceptable salts thereof as described above, together with one or more pharmaceutically acceptable excipients. The manidipine dihydrochloride used in the preparation of pharmaceutical compositions may substantially consist of one of forms I, II, III, IV or V described above, or may substantially consist of a combination of two or more of said forms. The manidipine based used in the preparation of pharmaceutical compositions may substantially consist of one of forms V or VI described above, or may substantially consist of a combination of both of said forms.

Manidipine or its salts have been found to be effective for the control of elevated blood pressure (hypertension). Pharmaceutical compositions according to the present invention comprise novel polymorphs I, II, III, IV, V, VI or VII of manidipne as an active ingredient together with one or more pharmaceutically acceptable carriers, excipients or diluents. Any conventional technique may be used for the preparation of pharmaceutical compositions and dosage forms according to the invention.

Manidipine polymorphs I, II, III, IV, V, VI and VII are useful for treating a variety of diseases and disorders, including: ankle edema. The drug also significantly lowers blood pressure in patients with hypertension and concomitant Type 2 diabetes mellitus or renal impairment, Accordingly, the present invention provides a method for treating a human suffering from a disease or a disorder known to be responsive to the administration of manidipine, by administering to said human, an effective amount of manidipine forms.

Various modifications may be made to the embodiments disclosed herein. Therefore the above description should not be construed as limiting, but should be considered as exemplification of mere embodiments.

EXAMPLES

The present invention will now be further illustrated by the following examples, which do not limit the scope of the invention in any way.

Example 1

Preparation of Manidipine Base

To a solution of benzhydryl piperazine (7.28 gm) in toluene (35 ml) at room temperature, dimethyl formamide (70 ml), 2-chloroethanol (5 ml) and potassium carbonate (5 gm) were added. The reaction mass was heated to reflux with constant stifling for 14-16 hours. Reaction mass was cooled, filtered, and concentrated under vacuum to get 2-(4-benzhydryl piperazine-1-yl) ethanol (yield: 7.5 gm).

To a suspension of 2,6-dimethyl-4-(3-nitro-phenyl)-1,4-dihydro-pyridine-3,5-dicarboxylic acid monomethyl ester (5 gm), dicyclohexyl carbodiimide (3.08 gm) and dimethylamino pyridine (0.25 gm) in toluene (30 ml) at room temperature was added 2-(4-benzhydryl piperazine-1-yl)ethanol (7.5 gm). Reaction mass was then heated to 70-75° C. for 2 hours. Reaction mass was then cooled to room temperature and filtered. Toluene layer was concentrated under vacuum to get manidipine base (5 gm).

Example 2

Preparation of Manidipine Dihydrochloride

Manidipine base was dissolved in acetone (15 ml). The pH of the solution was adjusted to 1-1.5 with IPA-HCl solution with constant stifling to get manidipine Dihydrochloride. The reaction mass was filtered and dried for 2 hours (yield: 3 gm).

Example 3

Preparation of Crystalline Form I of Manidipine Dihydrochloride

Manidipine Dihydrochloride (16 g) was dissolved in methanol (320 ml) at 65° C. The solution was cooled to room temperature with constant stifling for 4 hours. The solid obtained was filtered, washed with methanol and dried under vacuum at about 40-45° C. for 10-12 hours to yield crystals of Form I (Yield: 14.6 gm) (Purity: 99.81%)

The polymorph was characterized by XRD.

Example 4

Preparation of Crystalline Form II of Manidipine Dihydrochloride

Manidipine dihydrochloride (0.5 g) was dissolved in (1:1) mixture of methanol and denatured ethanol (8 ml) at 65° C. The clear solution was cooled slowly and stirred at room temperature for 12-14 hours. The solid obtained was filtered, washed with methanol and dried under vacuum at about 40-45° C. for 10-12 hours to yield crystals of form II. (Yield: 0.4 gm) (Purity: 99.89%)

The polymorph was characterized by XRD.

Example 5

Preparation of Crystalline Form III of Manidipine Dihydrochloride

Manidipine dihydrochloride (0.5 g) was dissolved in (1:1) mixture of methanol and toluene (4.5 ml) at 75° C. The clear solution was cooled slowly and stirred at room temperature for 12-14 hours. The solid thus obtained was filtered, washed with methanol and dried under vacuum at about 45° C. for 10-12 hours to yield crystals of form III. (Yield: 0.4 gm) (Purity: 99.81%)

The polymorph was characterized by XRD.

Example 6

Preparation of Crystalline Form IV of Manidipine Dihydrochloride

Manidipine dihydrochloride (0.5 g) was dissolved in toluene: denatured ethanol (1:1) mixture (9.5 ml) at 75-80° C. The clear solution was cooled slowly and stirred at room temperature for 12-14 hours. The solid obtained was filtered, washed with denatured ethanol and dried under vacuum at 45° C. for 10-12 hours to yield crystals of form IV. (Yield: 0.35 gm) (Purity: 99.87%)

The polymorph was characterized by XRD.

Example 7

Preparation of Amorphous Form V of Manidipine Dihydrochloride

Manidipine dihydrochloride (1 g) was dissolved in methanol (20 ml) at 65° C. The solvent was distilled off completely under vacuum below 50° C. Solid obtained was dried under vacuum at 40-45° C. for at least 10 hours to yield amorphous form V. (Yield: 0.9 gm) (Purity: 99.80%)

The amorphous form was characterized by XRD.

Example 8

Preparation of Crystalline Form VI of Manidipine Base

Manidipine base (1 g) was dissolved in methanol (2 ml) at 45° C. The solution was cooled to room temperature. N-heptane (20 ml) was added to the clear solution. Stirring was continued for 10-12 hours and precipitate was filtered and washed by n-heptane. Isolated compound was dried under vacuum at 45-50° C. for 10-12 hours. (Yield: 0.8 gm) (Purity: 99.79%)

The polymorphic form VI was characterized by XRD.

Example 9

Preparation of Amorphous Form VII of Manidipine Base

Manidipine base (1 g) was dissolved in methylene dichloride (5 ml) at 60° C. The solvent was distilled off completely. The compound thus obtained was isolated and dried under vacuum at 45-50° C. for 10-12 hours. (Yield: 0.9 gm) (Purity: 99.77%)

The amorphous form VII was characterized by XRD.

The invention claimed is:

1. Non-hygroscopic crystalline Form I of manidipine dihydrochloride in the form of racemate, characterized by having a XRD pattern compromising peaks at 10.94, 13.5, 20.90, 21.14 and 24.86±0.2 °2θ.

2. Crystalline Form I of manidipine dihydrochloride according to claim 1, characterized by having an XRD pattern compromising further peaks at 13.82 26.40, 20.72, 24.50 and 24.58 °2θ±0.2 °2θ.

3. A process for preparing crystalline Form I of manidipine dihydrochloride according to claim 1, the process compromising dissolving manidipine dihydrochloride in methanol at reflux, cooling the reaction mass to a temperature ranging from about 25° C. to 30° C., isolating the precipitated crystalline Form I of manidipine dihydrochloride and drying under vaccum at about 40-45° C. for at least 10 hours.

4. The process according to claim 3, wherin the manidipine dihydrochloride used to prepare the Form I manidipine dihydrochloride is in any polymorphic form or in a mixture of any polymorphic forms.

5. A pharmaceutical composition comprising a crystalline Form I of manidipine dihydrochloride, optionally in combination with one or more pharmaceutical acceptable excipients.

* * * * *

UNITED STATES PATENT AND TRADEMARK OFFICE
CERTIFICATE OF CORRECTION

PATENT NO. : 9,018,376 B2  
APPLICATION NO. : 13/392583  
DATED : April 28, 2015  
INVENTOR(S) : Dharmaraj Ramachandra Rao, Rajendra Narayanrao Kankan and Maruti Ganpati Ghagare Page 1 of 1

It is certified that error appears in the above-identified patent and that said Letters Patent is hereby corrected as shown below:

In the claims:

Claim 2, Column 12, Line 22, replace "13.82 26.40, 20.72" with --13.82 16.40, 20.72--.

Signed and Sealed this  
First Day of September, 2015

Michelle K. Lee  
*Director of the United States Patent and Trademark Office*